(12) United States Patent
Epaules et al.

(10) Patent No.: US 7,455,694 B2
(45) Date of Patent: Nov. 25, 2008

(54) ACETABULAR CUP FOR A HIP PROSTHESIS

(75) Inventors: Arnaud Aux Epaules, Saint-aubin-sur-mer (FR); Jean-Pierre Brée, Fontaine Etoupefour (FR); Nicolas Delogé, Douvres-la-Delivrande (FR)

(73) Assignee: Benoist Girard SAS (FR)

( * ) Notice: Subject to any disclaimer, the term of this patent is extended or adjusted under 35 U.S.C. 154(b) by 7 days.

(21) Appl. No.: 11/581,910

(22) Filed: Oct. 17, 2006

(65) Prior Publication Data

US 2007/0191961 A1 Aug. 16, 2007

(30) Foreign Application Priority Data

Oct. 20, 2005 (GB) .................................. 0521406.9

(51) Int. Cl.
*A61F 2/32* (2006.01)

(52) U.S. Cl. ............... 623/22.15; 623/22.18; 623/22.21

(58) Field of Classification Search .............. 623/17.14, 623/22.11, 22.15–22.18, 22.21, 22.22–22.3, 623/22.4, 23.4

See application file for complete search history.

(56) References Cited

U.S. PATENT DOCUMENTS

2002/0116068 A1* 8/2002 McLean .................. 623/22.15

2004/0199257 A1 10/2004 Dooney
2005/0228502 A1 10/2005 Deloge et al.

FOREIGN PATENT DOCUMENTS

| EP | 1 582 182 | 10/2005 |
| FR | 2807315 | 10/2001 |
| WO | WO-01/76511 | 10/2001 |
| WO | WO-02/058597 A | 8/2002 |

* cited by examiner

*Primary Examiner*—Bruce E Snow
*Assistant Examiner*—Megan Wolf
(74) *Attorney, Agent, or Firm*—Lerner, David, Littenberg, Krumholz & Mentlik, LLP (57) ABSTRACT

A hip prosthesis has a cup element having a part-spherical inner bearing surface and a spherical center through which the plane of a diametrical equator extends, and a ball shaped head which has a diameter to cooperate with the inner bearing surface to allow movement therein. The cup has a flat cordal lower surface parallel to the plane of an equator of the ball. The inner bearing surface has two or more equally spaced extension portions which extend beyond the diametrical equator towards the mouth of the cup. The surfaces of the two or more portions are relieved to enable the ball shaped head to be inserted into the cup by moving the flat on the ball across the face of one of the bearing surface extension portions and then rotating ball head to a position in which the flat on the ball head faces the mouth of the cup.

19 Claims, 7 Drawing Sheets

ACETABULAR CUP FOR A HIP PROSTHESIS

BACKGROUND OF THE INVENTION

This invention relates to an acetabular cup of a total hip prosthesis which comprises a cup having a part-spherical inner bearing surface and a ball shaped head mounted on a femoral component with a diameter to cooperate with said inner bearing surface to allow free movement therein.

The ball is designed to accept an attachment fitting for location in a socket in the ball and such a fitting can, for example, be a femoral stem. Cups of this type are known which comprise a single element made, for example, of a synthetic plastics material or metal, the inner bearing surface can also be formed as in insert which again can be of a synthetic plastics material, metal, ceramic or metal ceramic composite material and which is carried in an outer housing, the housing engaging the acetabulum with which it is to be used and be held in place by, for example, cement or mechanical means, for example, nails or screws.

In other known constructions of this type of cup the inner bearing surface can be provided on an inner layer or insert made from a different material than an outer backing which engages the acetabulum. Dual mobility cups generally comprise an inner bearing surface which receives the part-spherical ball head and which is itself freely mounted in a part-spherical element which has outer and inner bearing surfaces, the outer bearing surface engaging the inner bearing surface of an outer housing which engages the acetabulum. This type of cup allows greater mobility of angular movement and anti-dislocation characteristics.

In all these constructions, and, more especially, bi-polar or dual mobility cups, it is advantageous to have means for retaining the ball head against the inner bearing surface. There are various ways of achieving this, for example with a hard material, there are various ways of retaining the ball head inside the inner bearing surface. Deformable material cannot be used and in one arrangement a ring or circlet is used but this requires a third part and with a risk of wear. Another arrangement can consist of having two flats on the head and turning the head at 90° prior to inserting it into the cup and then again turning the head back through 90°. A disadvantage with this type of construction is that specific heads are required and there is risk of wear due to the truncating of the head. A system of this type is shown in FR 2 785 525 and 2 807 315.

The present Applicant's U.S. Publication 2005/0228502, the disclosure of which is incorporated herein by reference, also shows a construction of this type in which the inner bearing surface of the cup extends over an angle of more than 180°. A portion thereof adjacent an entry mouth is formed with a substantially flat face which is at a radius from the center of the hemispherical inner bearing surface which is less than the radius of the remainder. The ball head has a co-operating substantially flat face on its part-spherical surface on which is provided means to receive and retain the stem with which it is to be used, and the prior attachment of the stem allows the ball head to be located in the cup and rotated but it is retained therein. The dimensions and configurations of the part-spherical inner bearing surface and the part-spherical bearing surface of the head being arranged to cause a movement of translation of the head during insertion when fitting.

This type of construction, although it provides a crescent shaped retention area at each opposed side of the head, relies upon the substantially flat face which is at a radius from the center of the hemispherical bearing surface to retain the ball in place.

The present invention is intended to provide an improved construction which provides better location of the ball.

SUMMARY OF THE INVENTION

According to the present invention a total hip prosthesis comprises a cup having a part-spherical inner bearing surface and a spherical center through which the plane of a diametrical equator extends. A ball shaped head is provided which has a diameter to co-operate with the inner bearing surface to allow free movement therein, and having a flat cordal lower surface parallel to the plane of an equator of the ball. The inner bearing surface has two or more equally spaced extension portions which extend beyond the diametrical equator towards the mouth of the cup, and two or more extension portions below the diametrical equator. The surface between the extension portions are relieved to enable the ball shaped head to be inserted into the cup by moving the flat on the ball across the face of one of the bearing surface extension portions and then rotating ball head to a position in which the flat on the ball head faces the mouth of the cup. The ball head is held in the cup by the extension portions which extend beyond the said diametrical equator.

Thus, it will be appreciated that this arrangement provides two or more areas for retaining the ball shaped head in place.

In one preferred construction the inner bearing surface has two extension portions the diametrical distance between them being slightly more than the distance between the center of the cordal length of the flat on the ball head and the maximum distance from said flat to the outer curved surface of the ball head.

The extension portions can be diametrically opposite each other or they can be angled in relation to each other between 179° and 90°. Preferably the enclosed angle is 120°.

In another embodiment according to the invention the inner bearing surface has three extension portions which are spaced apart around the cup. The distance from the center of the cordal length of either of the other two extension portions is slightly more than the distance between the center of the cordal length of the flat on the ball head and the maximum distance from the flat to the outer curved surface of the ball head.

The three extension portions can be equally spaced apart or they can be asymmetrical. Preferably the enclosed angle between the extension portions is 120°.

The dimensions and configurations of the inner bearing and the ball head can be arranged to cause a movement of translation of the head during insertion to displace the ball head into the position in which it is retained by the extension portions.

The transverse axis of the mouth of the cup can be substantially parallel with the flat on the ball head when being inserted and is offset to the transverse axis of the inner bearing surface of the cup. This offset is preferably not more than 10 mm.

The inner bearing surface of the cup can be provided with an inner bearing layer and this can be in the form of an insert which can move within another bearing layer within a backing to provide a dual mobility cup.

In a construction of this kind the inner bearing surface of the other bearing layer can have two or more equally spaced extension portions which extend beyond its diametrical equator. The surfaces between the extension portions are relieved to enable the inner bearing layer to be inserted into the other bearing layer by moving the mouth of the inner bearing layer across the face of one of the bearing surface extension positions and then rotating the inner bearing layer insert to a position in which its mouth faces the mouth of the other bearing layer. The inner bearing layer insert is held in the other bearing layer by the extension portions which extend beyond the diametrical center.

Thus, this location arrangement between the inner bearing surface and the other bearing layer is similar to the location arrangement between the ball head the cup as set forth above. The cup can be adapted for location in an acetabulum with cement or, alternatively, without element.

The flat surface on the ball head can have a socket to receive a stem or other attachment fitting and such a fitting can be in the form of a femoral stem. The invention also includes a total hip prosthesis as set forth above which also incorporates an attachment fitting.

An advantage of the present invention is that some standard size ball heads can be used and entry into the cup can be closely controlled by the dimensions of extension portions so that the operation of the ball head against the bearing surface is accurate.

BRIEF DESCRIPTION OF THE DRAWINGS

The invention can be performed in various ways and some embodiments will now be described by way of example and with reference to the accompanying drawings in which.

DETAILED DESCRIPTION

In the construction shown in FIGS. 1 to 4 the invention is applied to a prosthetic femoral joint which comprises a part-spherical cup 1 which is made from a single material, for example a synthetic plastics material, and which is adapted for location in an acetabulum. The cup 1 has a part-spherical inner bearing surface 2 to receive a part-spherical ball head 3 (see FIG. 4) which can be attached to a stem 4 (see FIG. 25) for location in a femur. The stem 4 has a shoulder carrying a tapered spigot 5 which is adapted to locate and be maintained in a tapered socket 6 in the ball head. This method of attachment is well-known and the construction of the stem and the spigot are also known in themselves and will not be described further.

As will be seen from FIGS. 1 to 4 the inner bearing surface 2 extends around an angle of more than 180°. The spherical center of the part-spherical inner bearing surface is indicated by reference numeral C and through which the plane of a diametrical equator extends which is indicated by reference numeral E.

Figure 1:
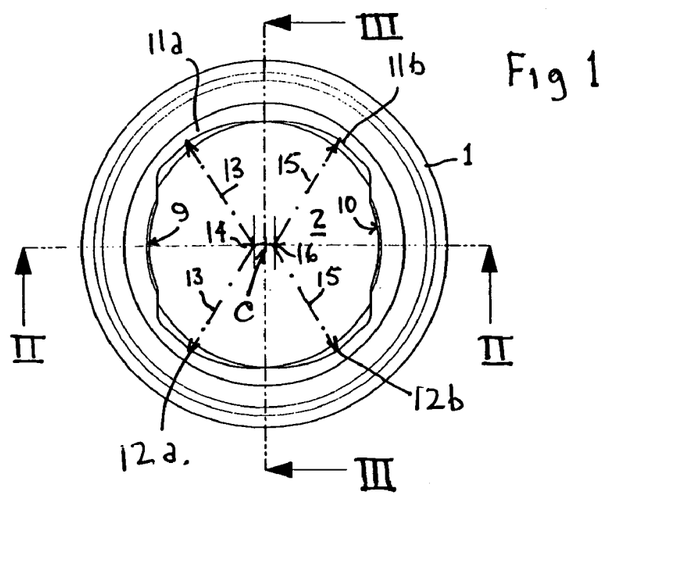
FIG. 1 is a diagrammatic plan view from below of a part-spherical acetabular cup embodying the invention and having two extension portions.

The inner bearing surface 2 has two diametrically spaced extension portions 9 and 10 which are also below the diametrical equator E and between these extension portions 9 and 10 the bearing surface on each side is relieved, as indicated by reference numeral 11 and 12. Each of the relievings 11 and 12 consist of two portions. On one side the relieving is provided by two part-cylindrical surfaces 11a, 11b and on the other side by part-cylindrical surfaces 12a, 12b. In FIG. 1 the radius of each of the surfaces 11a and 12a are indicated by broken line 13, the center of the radius being indicated by reference numeral 14. The radius of each of the two part-cylindrical portions 11ba and 12b is indicated by broken lines 15 and the center from which they extend by reference numeral 16.

From FIG. 1 it will be seen that the centers 14 and 16 are displaced laterally away from the spherical center C.

Figure 2:
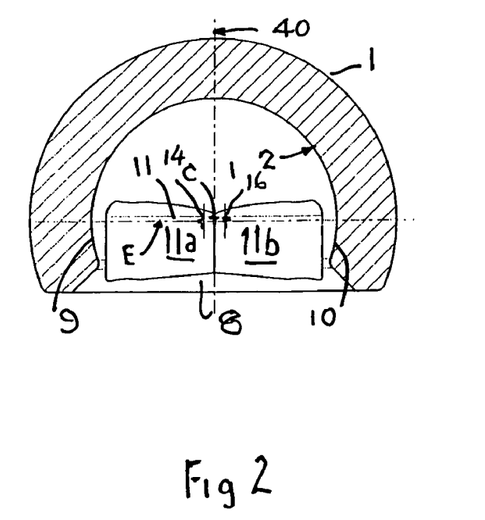
FIG. 2 is a cross-sectional side elevation on the line II-II of FIG. 1.
Figure 3:
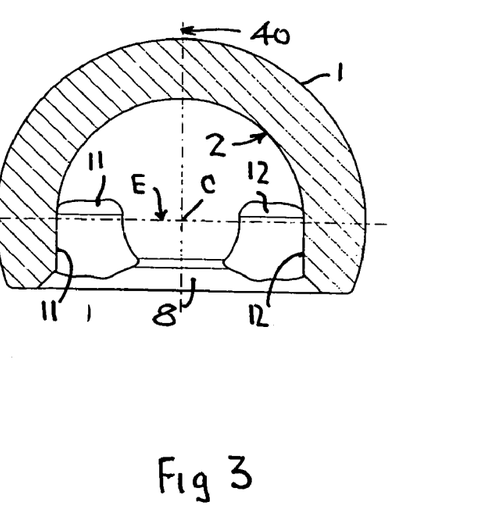
FIG. 3 is a cross-sectional side elevation on the line III-III of FIG. 1.

The length of the radii 13 and 15 are slightly more than the diameter of the ball head and each surface extends parallel to a main loading axis 40, as best shown in FIG. 2. It will also be seen that these part-cylindrical surfaces extend outwardly from the diametric equator E towards the mouth 8 of the cup. Each pair of surfaces 11a, 12a, and 11b, 12b, act to accept the adjacent diameter of the ball head 3 when initially inserted into the cup.

Figure 4:
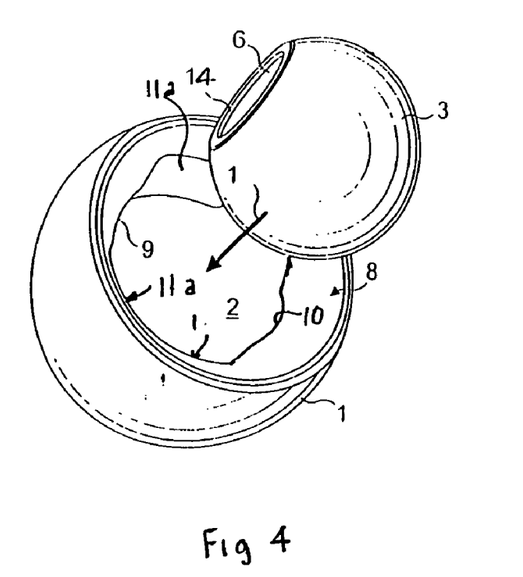
FIG. 4 is a diagrammatic exploded view showing how an unattached ball head is inserted into the cup shown in FIGS. 1 to 3 and with which it is to be used.

There is a slight movement of translation of the head during insertion to slightly displace it so that there is a crescent shaped location area on each side. The axes of the centers 14 and 16 are displaced from the main loading axis 40 (as shown in FIG. 2) so that when the ball is inserted, as shown in FIG. 4, the flat surface 14 of the ball is closely adjacent one of the portions 9 or 10 and appropriate part-cylindrical surfaces 11a, 12a or 11b, 12b allow it to pass into the cup. As the ball head passes beyond the diametrical equator E its part-spherical surface 3 engages the part-spherical surface 2 of the cup and the cup moves to either the right or left when viewed as in FIG. 1 so that there is a transitional movement of the ball head 3 into line with the main loading axis 40.

It will be appreciated that this translational movement will occur either to the right or to the left and when viewed in FIG. 4 will move to the right.

FIGS. 7 to 12 show the sequence of movement during insertion of the ball head.

Figure 7:
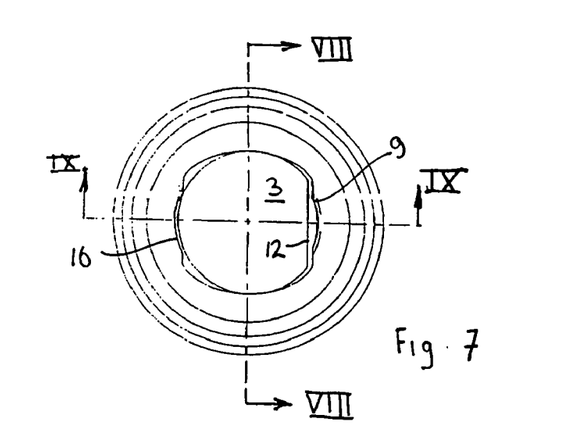
FIG. 7 is a plan view showing a cup, as shown in FIGS. 1 to 4, with a ball head in the entry position.
Figure 8:
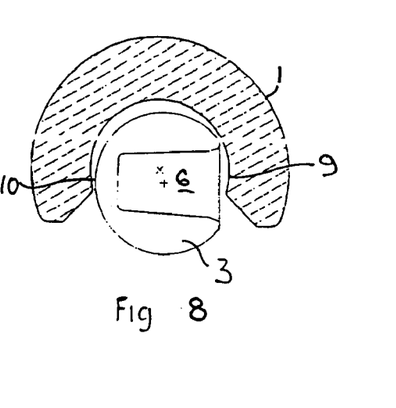
FIG. 8 is a diagrammatic cross-sectional view on the line VIII-VIII showing the ball head in the entry position.
Figure 9:
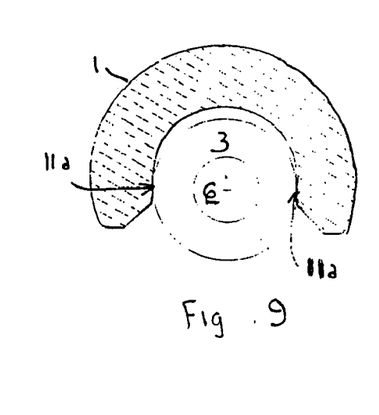
FIG. 9 is a diagrammatic cross-sectional view on the line IX-IX of FIG. 7 showing the ball head in the entry position.
Figure 10:
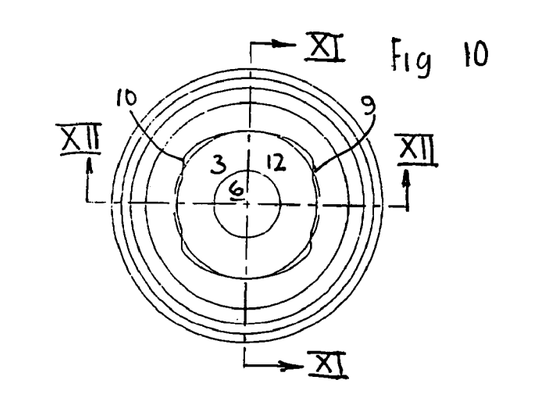
FIG. 10 is a plan view showing a ball head in its located position.

As shown in FIG. 7 the ball head 3 is in the entry position and is displaced slightly to the right due to the offset between the radius centers 14 and 16. From FIG. 9 it will be seen that the ball can pass between the appropriate surfaces 11a-12a or, appropriately 11b-12b, depending upon which side it is entered.

Figure 11:
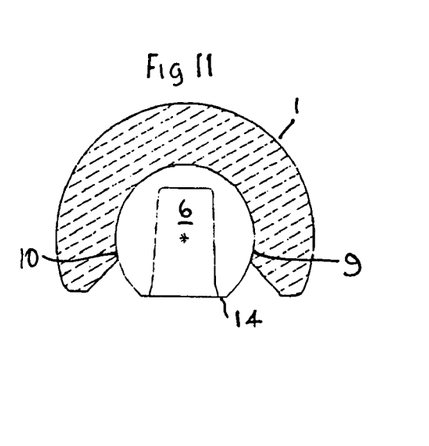
FIG. 11 is a diagrammatic cross-sectional view on the line XI-XI of FIG. 10 showing the ball head in its located position.
Figure 12:
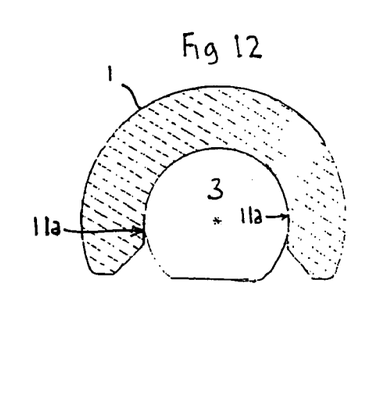
FIG. 12 is a diagrammatic cross-sectional view on the line XII-XII of FIG. 10 also showing the ball head in its location position.

When the ball has reached its seated position and has been rotated so that the flat surface 14 is parallel with the diametrical equator E the ball is fully seated, as shown in FIGS. 11 and 12. From FIG. 11 it will also be seen how the extension portions 9 and 10 hold the cup in position at two points spaced across its mouth.

When the stem 4 is inserted in position in the tapered socket 6 the removal of the free moving ball head is prevented.

The offset between the main loading axis 40 and the axes 14 or 16 can be up to 10 mm and is preferably about 2 or 3 mm.

As will be seen from FIG. 4 the ball head 3 has a co-operating substantially flat face 14 which is formed as a flat cordal lower surface parallel to the plane of an equator of the ball. Prior to the attachment of the ball head to the spigot 5 of the stem 4 flat surface 14 allows the ball to be located in the cup to a position in which the flat on the ball head faces the mouth 8 of the cup and the ball is then held in the cup by the extension portions 9 and 10 which extend beyond the diametrical equator E. The direction of entry of the ball head into the cup is indicated by arrow 16.

The spigot 5 can be locked into the ball head 3 at any time during the surgical proceedings, for example, the ball could be locked into the cup prior to assembly into the acetabulum, during assembly thereto, or after the cup has been cemented or held in position by any other means.

Figure 5:
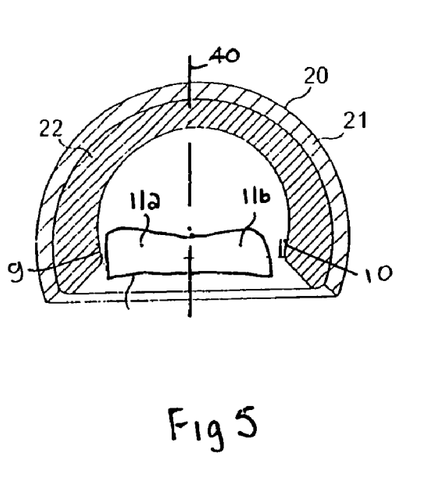
FIG. 5 is a diagrammatic cross-section of a cup, according to the invention, similar to that shown in FIGS. 1 to 4 provided with a backing.

FIG. 5 shows how the invention can be applied to a cup using a liner in a backing and the same reference numerals are used to indicate similar parts to those used in the other figures. In this construction the cup 20 comprises an outer backing 21 made from metal or synthetic plastics material or any other suitable material and is provided with a liner 22 again made from any suitable material, for example a synthetic plastics material, metal, ceramic or a metal ceramic composite material. The construction of the liner is similar to the construction of the cup shown in FIGS. 1, 2 and 3 and the invention is applied in the same way.

Figure 6:
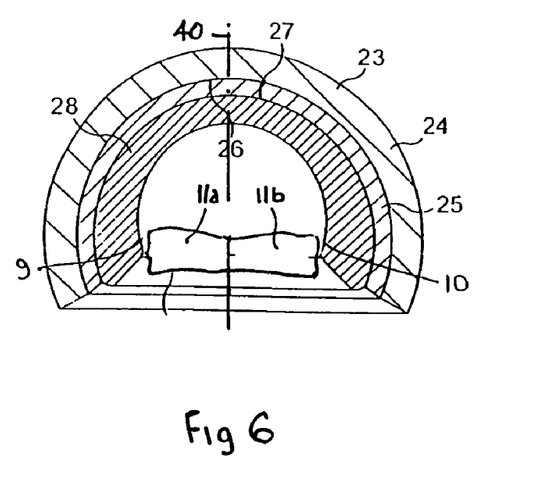
FIG. 6 is a diagrammatic cross-sectional view of a cup similar to that shown in the preceding figures and constructed as a dual mobility cup.

FIG. 6 shows how the invention can be applied to a dual mobility cup. Again the same reference numerals are used to indicate similar parts as the previous constructions but with this arrangement the cup comprises a backing 25 which has an outer bearing surface 26 and in which is retained a bearing insert 28, the construction being similar to that shown in FIG. 5. The outer backing 25 is located in an outer shell 23 and in which it can move. This type of dual mobility cup provides a greater range of movement for the joint.

In the construction shown in both FIG. 5 and FIG. 6 it will be seen that the method of entry of the ball head is similar to that described with regard to the preceding construction, shown in FIGS. 1 to 4.

Figure 13:
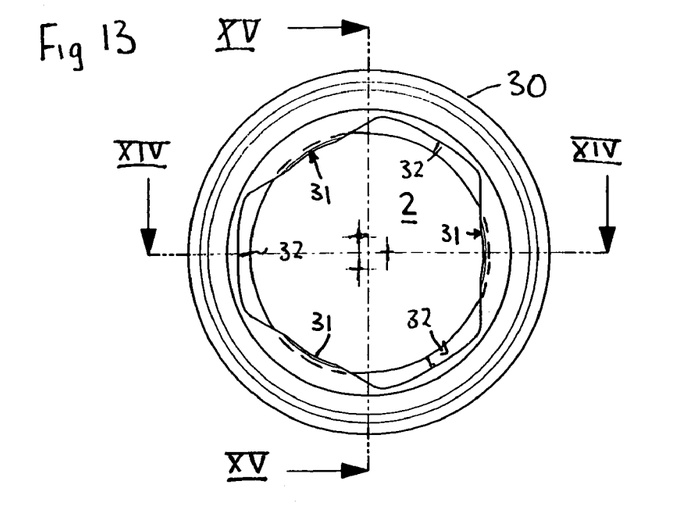
FIG. 13 is a plan view from below of an alternative construction of a cup, according to the invention, which has three equally spaced extension portions.
Figure 14:
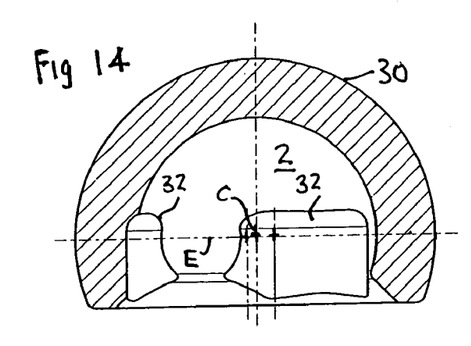
FIG. 14 is a diagrammatic cross-sectional view of the cup shown in FIG. 13 on the line XIV-XIV.
Figure 15:
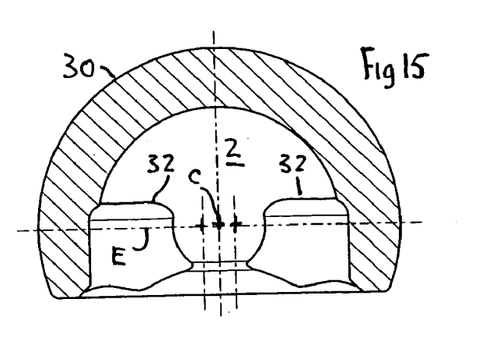
FIG. 15 is a diagrammatic cross-sectional side elevation of the cup shown in FIG. 13 on the line XV-XV.
Figure 16:
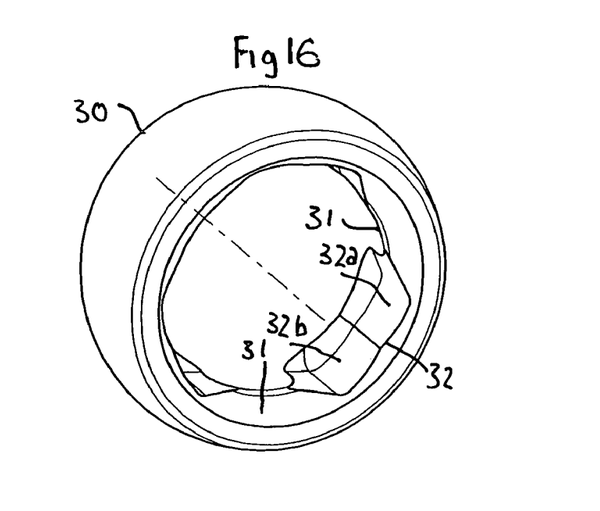
FIG. 16 is a diagrammatic isometric view of the cup shown in FIGS. 13, 14 and 15 from one side.

FIG. 13 is a plan view of an alternative construction of cup which is provided with three extension portions. In this arrangement the cup 30 has an inner bearing surface 2 and three extension portions 31 are provided which are equally spaced apart around the cup. The distance from the center of the cordal length of each extension portion 31 to the center of the center of the cordal length of either of the other two extension portions is slightly more than the distance between the center of the cordal length of the flat 14 on the ball head and the maximum distance from said flat to the curved outer surface of the ball head itself. Three relieved portions are provided, each portion being indicated by the general reference numeral 32. Each relieved portion comprises two portions 32a and 32b. Each of these portions 32a and 32b is part-cylindrical, the radius of which is most clearly shown in FIG. 18. Thus each relieved portion 32 has two curved part-cylindrical surfaces 32a, 32b. As will be seen from FIG. 19 the centers of the radii are offset from the center C and are equally spaced around a circumference with a radius of up to 10 mm and preferably about 2 or 3 mm.

As these centers of radii are offset there will be translation movement on entry of the bore in any of the three directions, depending upon the center of offset. The advantage of this construction is that it provides additional contact surface to retain the ball in position over the construction shown in FIGS. 1 to 4.

Figure 17:
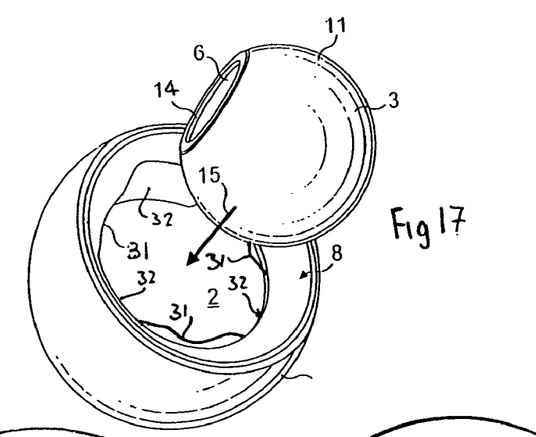
FIG. 17 is a diagrammatic exploded view showing how the ball is inserted into the cup shown in FIGS. 13 to 16.

FIG. 17 shows how the ball can be inserted into the cup by moving the flat 12 on the ball across the face of one of the bearing extension portions 31 and then rotating the ball head to a position in which the flat 12 on the ball faces the mouth of the cup. Thus the ball head is again held by the extension portions 31 which extend beyond the said diametrical equator of the inner bearing surface.

Figure 19:
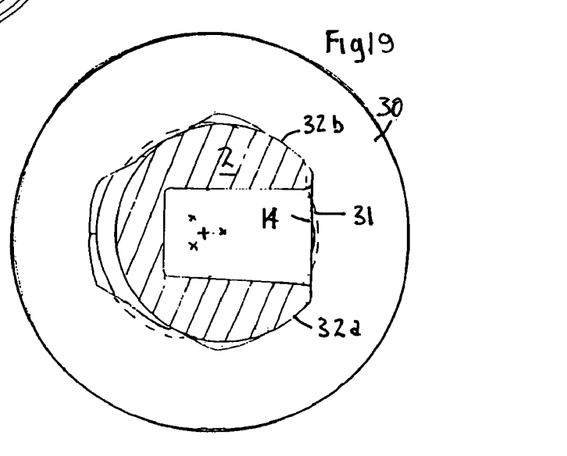
FIG. 19 is a view similar to FIG. 18 showing a ball head in the entry position.
Figure 20:
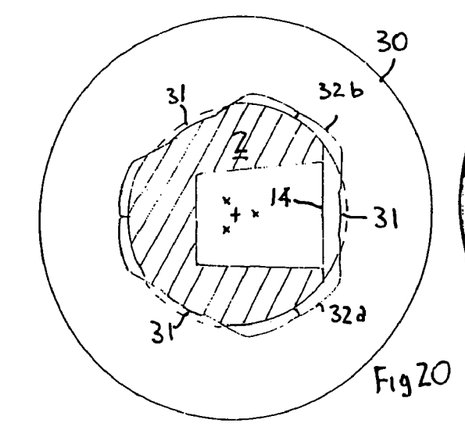
FIG. 20 is a view similar to FIG. 19 but showing the ball head in the inserted position.
Figure 21:
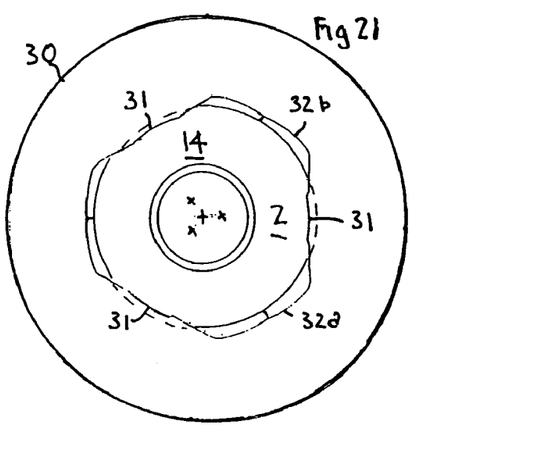
FIG. 21 shows the ball head in the entry position and after rotation to its operative position.
Figure 22:
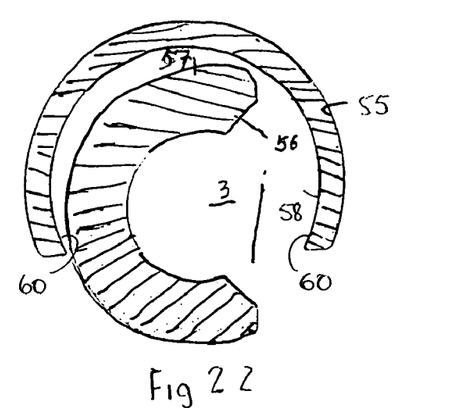
FIG. 22 is a diagrammatic cross-section from one side of a dual mobility type prosthesis incorporating the present invention.

FIGS. 19, 20 and 21 show how the ball head 3 is located in the cup. FIG. 19 shows the ball head 3 in the entry position with the flat 14 on the ball head passing across the face of an extension portion 31. The shape of the ball head is accommodated in the cup due to the relieved portions 32b and 32a. The head 3 can now move further into the cup with a translational movement to the left as shown in FIG. 20 to take up a central position. FIG. 21 shows the ball head when rotated so that its flat 14 faces toward the mouth of the cup and is ready to receive a stem 4.

Figure 18:
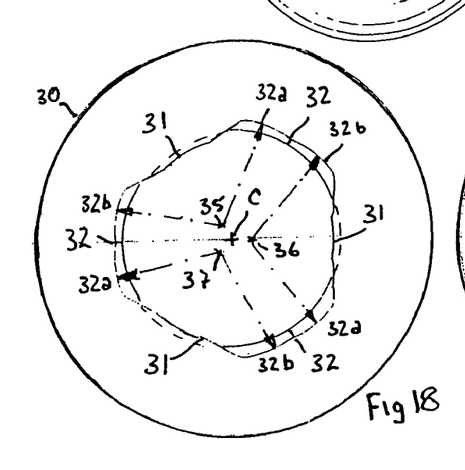
FIG. 18 is a plan view from below similar to FIG. 13 but showing the configuration of the relieved portions of the bearing surface.

Translation of movement can again be arranged in any of the three directions and the three centers of offset, one from each of the appropriate relieved portions, are indicated by reference numerals 353, 36 and 37 in FIG. 18. The central axis is indicated by letter C.

FIGS. 22 to 25 show a construction of a dual mobility cup according to the invention. In this construction an outer shell 55 is provided within which is a freely movable inner bearing liner 56. The ball head is held in a similar manner to the construction as described above but with this arrangement the inner bearing member 56 also has an outer bearing surface 57 which engages the inner bearing member 58 of the outer shell 55. The inner bearing surface of the outer shell 55 can be provided with two or more equally spaced extension portions which extend beyond its diametrical equator toward its mouth and two or more relieved portions, indicated by reference numeral 59 in FIG. 23. A construction using two extension portions is shown in FIGS. 21 to 25. The surfaces of these relieved portions enable the inner bearing layer 56 to be inserted into the outer housing 55 by moving the mouth of the inner bearing layer 56 across the face of one of the bearing surface extension portions, indicated by reference numeral 60, and then rotating the inner bearing layer 56 to a position in which its mouth faces the mouth of the housing 55 and the inner bearing layer 56 is then held by the bearing layer by the extension portion 60 which extend beyond its diametrical center.

Figure 23:
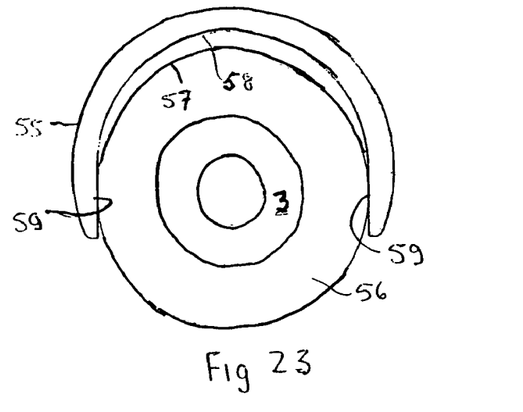
FIG. 23 is a diagrammatic cross-section of the cup shown in FIG. 22.
Figures 24, 25:
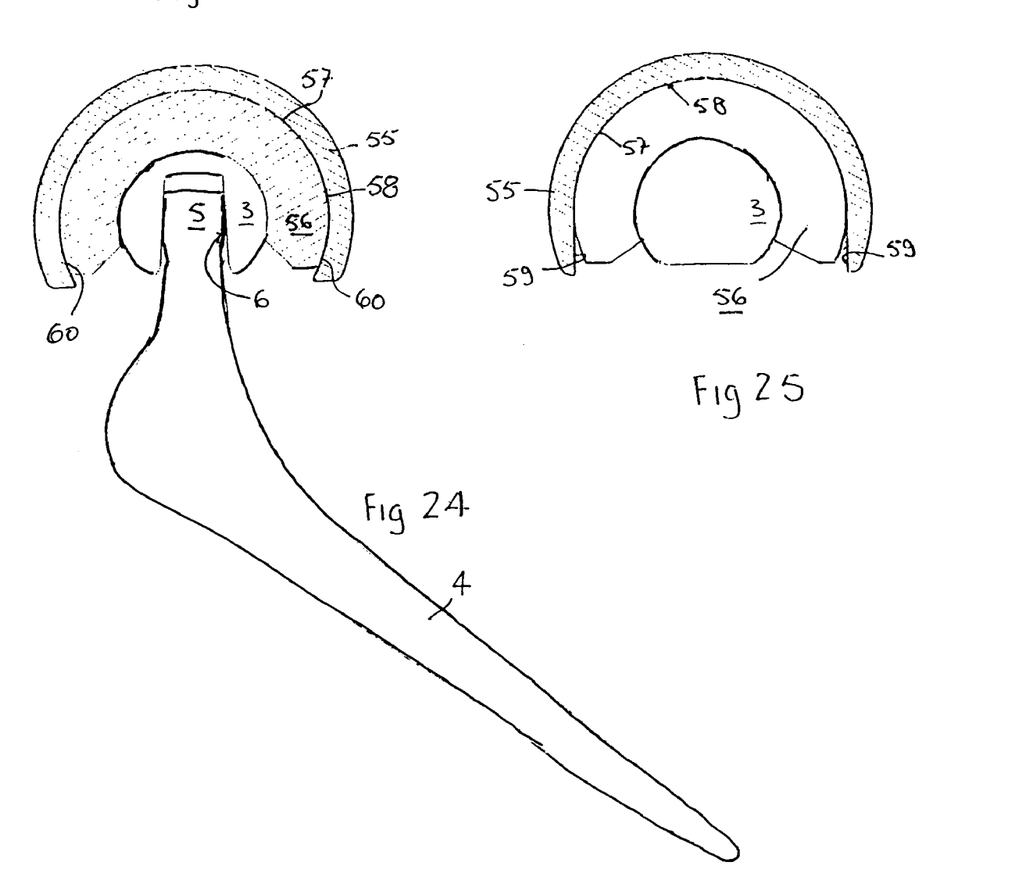
FIG. 24 is a diagrammatic cross-sectional showing the cup shown in FIG. 22 with the ball head and inner liner in the located position and the attachment stem in place.
FIG. 25 is a diagrammatic end cross-section of the joint shown in FIG. 22.

Thus, the construction is similar to that described in the other figures with regard to the connection of the ball head and the inner bearing layer. FIG. 23 shows how the construction is finally assembled and with the stem 4 in position and FIG. 24 shows the parts assembled as a cross-sectional end view.

Figure 26:
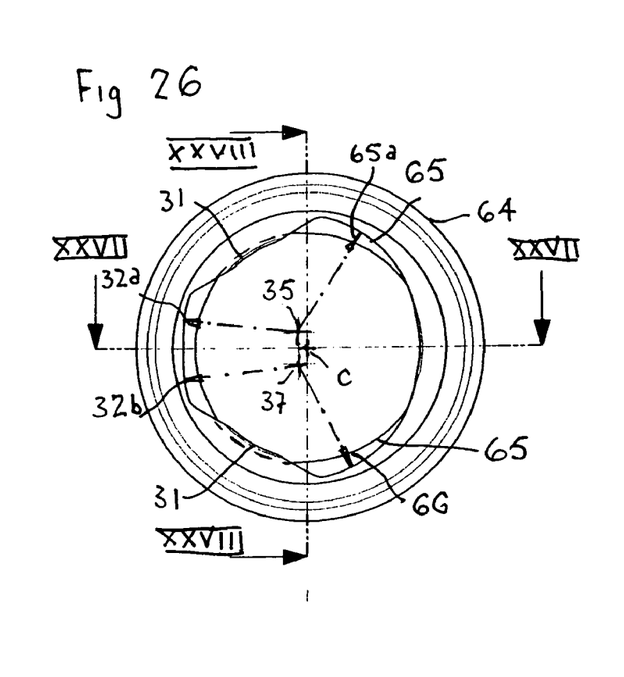
FIG. 26 is a plan view of another alternative construction of a cup according to the invention which has two extension portions which are angled in relation to each other.
Figure 27:
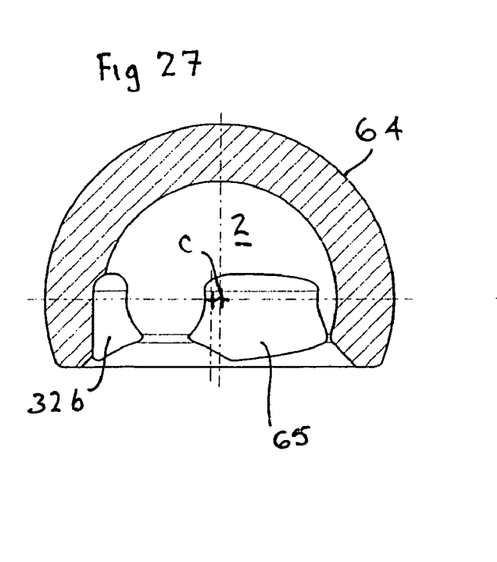
FIG. 27 is a diagrammatic cross-sectional view of the cup shown in FIG. 26 on the line XXVII-XXVII.
Figure 28:
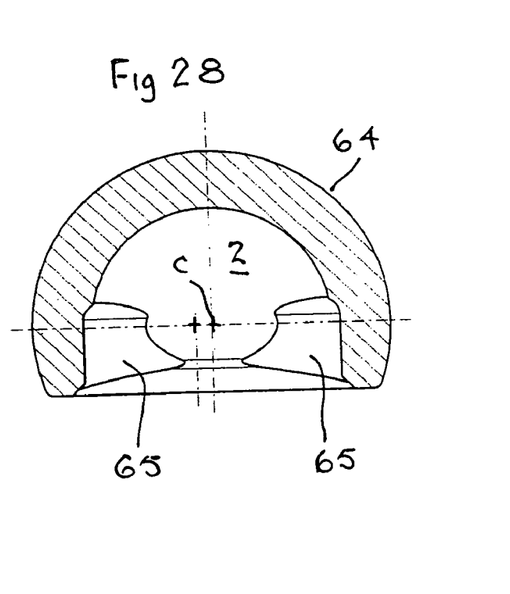
FIG. 28 is a cross-sectional side elevation of the cup shown in FIG. 26 on the line XXVIII-XXVIII.

FIGS. 26, 27 and 28 show another construction, according to the invention, in which a cup 64 has two spaced apart extension portions but they are not diametrically opposite each other. This construction is similar to the three extension portion construction shown in FIGS. 13 to 21 minus one of the extension portions. The same reference numerals are therefore used to indicate similar parts to those shown in FIGS. 13 to 21. The two extension portions 31 in this construction are spaced apart by an enclosed angle of 120° but in this construction only the relieved portion 32 at the left hand side of the drawing has two portions 32a, 32b. The remaining relieved portions indicated by reference numeral 65 consists of a single relieving 55a taken from the center 35 and a single relieving 66 taken on the other side of the cup from the center 37. The relievings are therefore similar to those employed in the embodiments described above. The enclosed angle between the extension portions 31 can be set to any appropriate angle which is convenient. The type of construction shown in FIGS. 26, 27 and 28 can be employed in the construction shown in FIGS. 22 to 25.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A total hip prosthesis comprising a cup having a part-spherical inner bearing surface and a spherical center through which the plane of a diametrical equator extends, and a ball shaped head which has a diameter to co-operate with said inner bearing surface to allow free movement therein, and having a flat cordal lower surface parallel to the plane of an equator of the ball, the ball-shaped head outer surface being ball-shaped at all locations spaced from the flat cordal lower surface; and in which the inner bearing surface has at least two equally spaced extension portions which extend beyond the diametrical equator toward the mouth of the cup, and two or more portions extending below the diametrical equator and between the extension portions, the surfaces of which are relieved by being curved in a radial direction parallel to the equator to enable the ball shaped head to be inserted into the cup by moving the flat on the ball across the face of one of the bearing surface extension portions and the ball-shaped head across the opposite curved relieved portion and then rotating ball head to a position in which the flat on the ball head faces the mouth of the cup and the ball head is held in the cup by the extension portions which extend beyond the said diametrical equator.

2. The total hip prosthesis as claimed in claim 1 in which the inner bearing surface has two extension portions the diametrical distance between them being slightly more than the distance between the center of the cordal length of the flat on the ball head and the maximum distance from the flat to the outer ball-shaped surface of the ball head.

3. The total hip prosthesis as claimed in claim 2 in which the extension portions are diametrically opposite each other.

4. The total hip prosthesis as claimed in claim 1 in which there are four extensions portions angled at 90° in relation to each other.

5. The total hip prosthesis as claimed in claim 1 in which there are three extension portions 120° apart.

6. The total hip prosthesis as claimed in claim 1 in which the inner bearing surface has three extension portions which are spaced apart around the cup and the distance from the center of the cordal length of each extension portion to the center of the cordal length of each extension portion to the center of the cordal length of either of the other extension portions is slightly more than the distance between the center of the cordal length of the flat on the ball head and the maximum distance from said flat to the outer curved surface of the ball head.

7. The total hip prosthesis as claimed in claim 6 in which the three extension portions are equally spaced apart.

8. The total hip prosthesis as claimed in claim 7 in which the enclosed angle between the extension portions is 120°.

9. The total hip prosthesis as claimed in claim 1 in which the dimensions and configuration of the inner bearing surface and the ball head are arranged to cause a movement of translation of the head in the radial direction and perpendicular to a plane through a center of the relieved surfaces and perpendicular to the plane of the equator during insertion to displace the ball head into the position in which it is retained by the extension portions.

10. The total hip prosthesis as claimed in claim 9 in which the transverse axis of the mouth of the cup is substantially parallel with the flat on the ball head when being inserted and is offset from the transverse axis of the inner bearing surface of the cup.

11. The total hip prosthesis as claimed in claim 10 in which the offset is not more than 10 mm.

12. The total hip prosthesis as claimed in claim 1 in which the inner bearing surface of the cup is provided on an inner bearing layer.

13. The total hip prosthesis as claimed in claim 12 in which the inner bearing layer is formed as an insert which can move within another bearing layer within a backing to provide a dual mobility cup.

14. The total hip prosthesis as claimed in claim 13 in which the inner bearing surface of said other bearing layer has two or more equally spaced extension portions which extend beyond its diametrical equator towards its mouth and two or more portions, also above its diametrical equator and between said extension portions, the surfaces of which are relieved to enable the inner bearing layer to be inserted into said other bearing layer by moving the mouth of the inner bearing layer across the face of one of the bearing surface extension positions and then rotating the inner bearing layer insert to a position in which its mouth faces the mouth of the said other bearing layer and the inner bearing layer is held in said other bearing layer by the extension portions which extend beyond said diametrical center.

15. The total hip prosthesis as claimed in claim 1 in which the cup is adapted for location in an acetabulum with cement.

16. The total hip prosthesis as claimed in claim 1 in which the cup is adapted for location in an acetabulum without cement.

17. The total hip prosthesis as claimed in claim 1 in which the flat surface on the ball head has a socket to receive a stem or other attachment fitting.

18. The total hip prosthesis as claimed in claim 17 which incorporates a stem or other an attachment fitting located in or for location in said socket.

19. A total hip prosthesis comprising:
a stem having a conical trunion at a proximal end;
a part-spherical head having a single flat cordal end including a bore for receiving the conical trunion, the head being spherically shaped in all areas other than the single flat cordal end; and
a cup having a part-spherical inner bearing surface for rotatably receiving the part-spherical head, the part-spherical cup inner surface having a center through which an equator of the part-spherical surface passes, the cup having a part-spherical extension portion extending beyond the equator toward an open end thereof, the extension portion including at least two recessed areas having end surfaces extending intermediate the equator and an end surface of the extension portion in a non-recessed area, the at least two recessed areas each have curved relieved portions extending along a plane parallel to a plane formed by the equator of the cup that slidingly receives a spherically shaped portion of the head and wherein the head is retained by the extension portions.

* * * * *

UNITED STATES PATENT AND TRADEMARK OFFICE
CERTIFICATE OF CORRECTION

PATENT NO. : 7,455,694 B2
APPLICATION NO. : 11/581910
DATED : November 25, 2008
INVENTOR(S) : Arnaud Aux Epaules, Jean-Pierre Brée and Nicolas Delogé

It is certified that error appears in the above-identified patent and that said Letters Patent is hereby corrected as shown below:

Title page, Item (57) Abstract, line 13, "rotating ball" should read --rotating the ball--.
Column 1, line 15, "in insert" should read --an insert--.
Column 1, line 60, "being arranged" should read --are arranged--.
Column 1, line 11, "having a flat" should read --also has a flat--.
Column 1, line 20, "rotating ball" should read --rotating the ball--.
Column 3, line 7, "head the cup" should read --head and the cup--.
Column 3, line 9, "without element" should read --without cement--.
Column 4, line 54, "consist of" should read --consists of--.
Column 4, line 57, "12a are indicated" should read --12a is indicated--.
Column 4, line 65, "length" should read --lengths--.
Column 5, line 3, "12b, act to" should read --12b, acts to accept--.
Column 7, line 23, "but they are" should read --which are--.
Column 7, line 32, "65 consists" should read --65 consist--.
Column 8, line 9, "then rotating" should read --then rotating the--.
Column 8, line 24, "four extensions portions" should read --four extension portions--.
Column 8, line 31, delete the entire line beginning with the word "center" and ending with the word "the".
Column 10, line 17, "each have curved" should read --each having curved--.

Signed and Sealed this

First Day of June, 2010

David J. Kappos
*Director of the United States Patent and Trademark Office*